US006861689B2

(12) United States Patent
Burnett

(10) Patent No.: US 6,861,689 B2
(45) Date of Patent: Mar. 1, 2005

(54) ONE TRANSISTOR DRAM CELL STRUCTURE AND METHOD FOR FORMING

(75) Inventor: James D. Burnett, Austin, TX (US)

(73) Assignee: Freescale Semiconductor, Inc., Austin, TX (US)

( * ) Notice: Subject to any disclaimer, the term of this patent is extended or adjusted under 35 U.S.C. 154(b) by 139 days.

(21) Appl. No.: 10/290,904

(22) Filed: Nov. 8, 2002

(65) Prior Publication Data

US 2004/0089890 A1 May 13, 2004

(51) Int. Cl.⁷ .............................................. H01L 27/108
(52) U.S. Cl. ................. 257/296; 257/314; 257/E27.085
(58) Field of Search ................................ 257/296, 314, 257/E27.085

(56) References Cited

U.S. PATENT DOCUMENTS

| | | | |
|---|---|---|---|
| 5,245,208 A | 9/1993 | Eimori | |
| 5,448,513 A | 9/1995 | Hu | |
| 5,548,150 A | 8/1996 | Omura | |
| 5,798,965 A | 8/1998 | Jun | |
| 6,238,967 B1 | 5/2001 | Shiho | |
| 6,621,725 B2 * | 9/2003 | Ohsawa | 365/150 |
| 6,661,042 B2 * | 12/2003 | Hsu | 257/239 |
| 2002/0051378 A1 | 5/2002 | Ohsawa | |
| 2002/0140044 A1 | 10/2002 | Manabe | |

FOREIGN PATENT DOCUMENTS

EP      0481559 A2   4/1992

OTHER PUBLICATIONS

Fazan et al., "A Highly Manufacturable Capacitor–Less 1T–DRAM Concept," SPIE Conference 2002, 14 pages.
Fazan et al., "A Simple 1–Transistor Capacitor–Less Memory Cell for High Performance Embedded DRAMs," IEEE 2002 Custom Integrated Circuits Conference, pp. 99–102.
"Memory Design Using One–Transistor Gain Cell on SOI," ISSCC 2002/Session 9/DRAM and Ferroelectric Memories/ 9.1; 8 pages.
Okhonin et al., "A Capacitor–Less 1T–DRAM Cell," IEEE Electronic Device Letters, vol. 23, No. 2, Feb. 2002, pp. 85–87.
Okhonin et al., "A SOI Capacitor–less 1T–DRAM Concept," 2001 IEEE International SOI Conference, pp. 153–154.
Nishiyama et al., "Suppression of the Floating–Body Effect in Partially–Depleted SOI MOSFET's with SiGe Source Structure and Its Mechanism," IEEE Transactions on Electronic Devices, vol. 44, No. 12, Dec. 1997, pp. 2187–2192.

* cited by examiner

Primary Examiner—David Nelms
Assistant Examiner—Tu-Tu Ho
(74) Attorney, Agent, or Firm—James L. Clingan, Jr.; Daniel D. Hill

(57) ABSTRACT

A single transistor DRAM cell is formed in a SOI substrate so that the DRAM cells are formed in bodies that are electrically isolated from each other. Each cell has doped regions that act as source and drain contacts. Between the drain contact and the body is a region, which aids in impact ionization and thus electron/hole formation during programming that is the same conductivity type as the body but of a higher concentration than the body. Adjacent to the source contact and to the body is a region, which aids in diode current during erase, that is the same conductivity type as the source contact but of a lower concentration than the source contact.

32 Claims, 7 Drawing Sheets

ONE TRANSISTOR DRAM CELL STRUCTURE AND METHOD FOR FORMING

FIELD OF THE INVENTION

The present invention relates to dynamic random access memory (DRAM) cells, and more particularly to DRAM cells not requiring a separate capacitor.

RELATED ART

DRAMs in general have enjoyed great success primarily due to the high density with good speed. In the quest for even higher density, a technique for single transistor DRAMs has been developed. The individual cell is provided in a semiconductor on insulator (SOI) substrate and requires only a single transistor, doing away with the need for the capacitor that has historically been used in DRAMs. These types of DRAM cells are also known as capacitorless DRAM cells because of not requiring a capacitor. In such a single transistor DRAM cell, the body of the transistor is left floating and, because it is on an SOI substrate so that the bodies of the transistors are isolated from each other, charge is accumulated in the body. This alters the threshold of the transistor, and such difference can be detected.

The technique for writing is, for N channel transistors that is the typical case, to generate holes that remain trapped in the body of the transistor, which is electrically floating. This is achieved by selecting the gate voltage so that the transistor operates to achieve greater hole/electron pair generation than removal of the holes. For erasing, the holes are removed also by adjusting the gate voltage so that hole removal occurs faster than hole/electron pair generation. One of the difficulties has been in achieving both writing and erasing with sufficient speed. If the hole removal is not sufficiently faster than hole/electron pair generation in the erase mode, then erase is too slow. Similarly, if in the write mode the hole/electron generation is not sufficiently faster than the hole removal, the write is too slow. This has been the problem, getting sufficient speed for both read and write. Thus, there is a need to find a technique for achieving sufficient speed for both read and write.

DETAILED DESCRIPTION

In one embodiment, a single transistor DRAM cell is a transistor formed in a SOI substrate so that the DRAM cells are formed in bodies electrically isolated from each other. Each cell has doped regions that act as source and drain contacts. Adjacent to one of the source and drain contacts and to the body is a region of the same conductivity type as the body but of a higher concentration. Also adjacent to one of the source and drain contacts and to the body is a region of the same conductivity type as the source and drain contacts but of a lower concentration. This is better understood with reference to the drawings and the following description.

Figure 1:
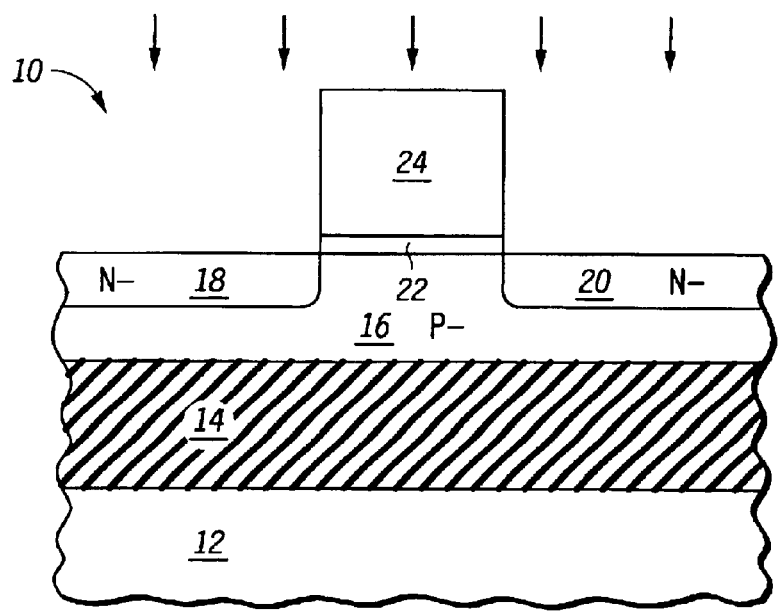
FIGS. 1–4 illustrate sequential cross sectional views of a semiconductor device made in accordance with one embodiment of the present invention.

Shown in FIG. 1 is a device structure 10 formed in a SOI substrate comprising a substrate 12, an insulator 14 on substrate 12, a body region 16 over insulator 14, a doped region 18, a doped region 20, a gate dielectric 22, and a gate 24. Doped regions 18 and 20 are doped to N− by an implant using gate 24 as a mask. This implant is chosen to be of a sufficiently low power so the resulting doped region does not reach all the way to the insulator 14. The gate can be of an appropriate material. Most commonly, gates are made from polysilicon. Similarly, gate dielectric 22 may be of any suitable material. Most commonly, gate dielectrics are thermally grown oxide. Body 16 is a semiconductor material and is most commonly now silicon. The dopant for N-type is typically phosphorus or arsenic.

Figure 2:
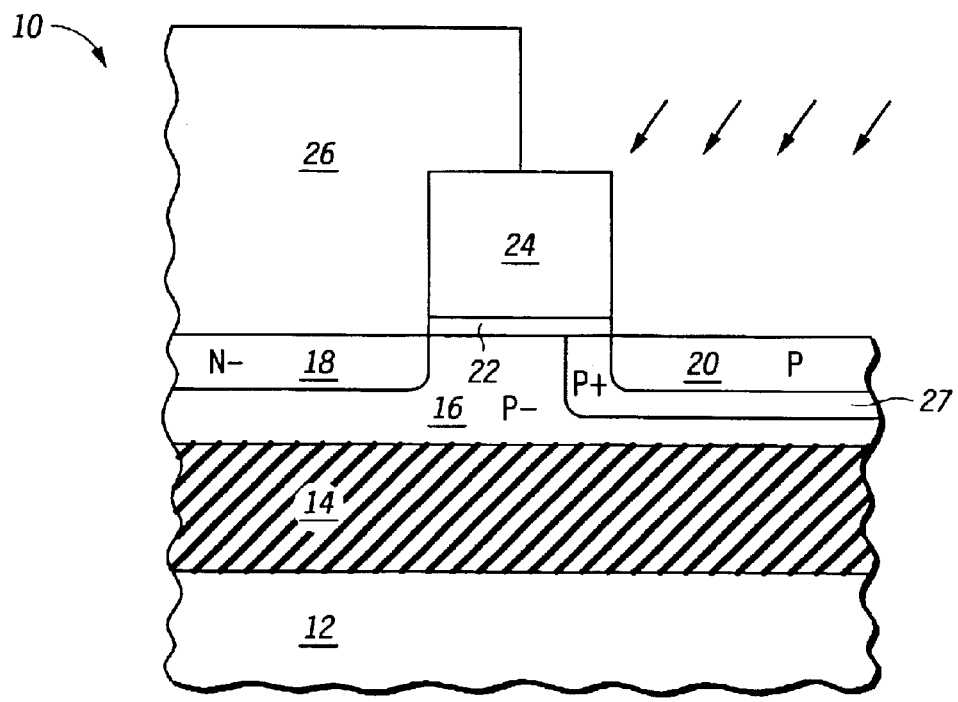

Shown in FIG. 2 is device structure 10 after a mask 26 has been formed over a portion of gate 24 and doped region 18 and after an angled implant of P-type material has been performed. Photoresist is the preferred mask but other masks that can form this function would acceptable. The angled implant, about 25 degrees from vertical, is similar to the halo implant that is commonly performed for transistors to reduce problems with punchthrough. In this case the resulting doped region 27 reaches to the surface of body 16 as shown in a region underlapping gate 24 and is also below doped region 20. This is achieved by using a lower energy than would be used if a halo implant were being used simply to reduce punchthrough. Also this implant changes doped region 20 from N-type to P-type with a net doping less than that of region 27.

Figure 3:
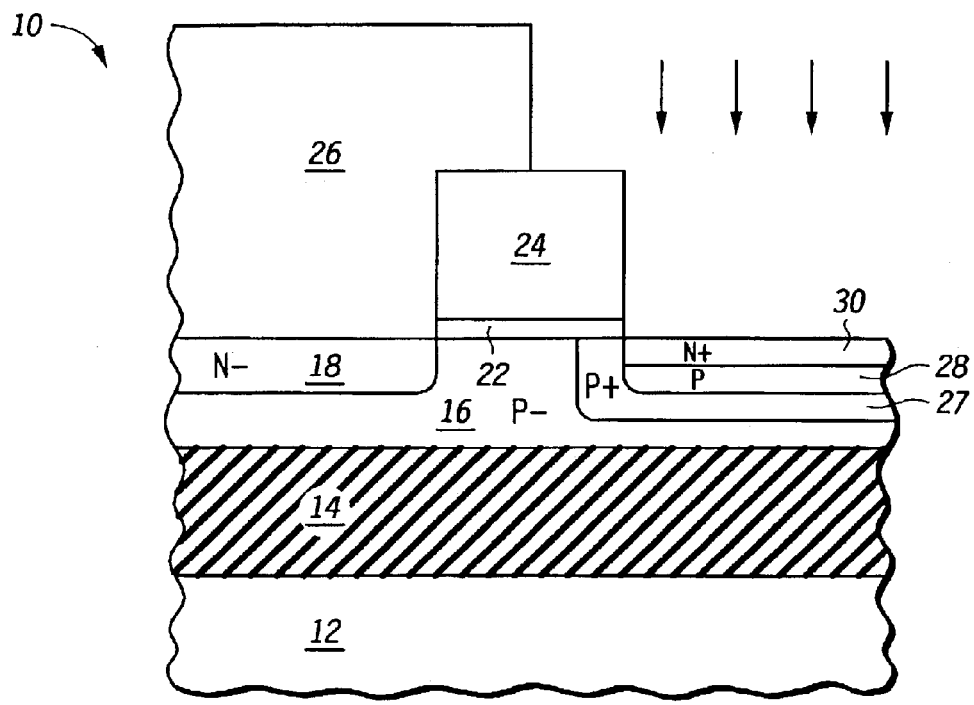

Shown in FIG. 3 is device structure 10 after a vertical N-type implant is performed. This implant also utilizes mask 26 to block the implant from doped region 18. The result of this implant is to form a doped region 30 that is N-type and leave a doped region 28 at P-type. Doped region 28 is a remaining portion of region 20 shown in FIG. 2 that is under doped region 30. This a relatively shallow implant.

Figure 4:
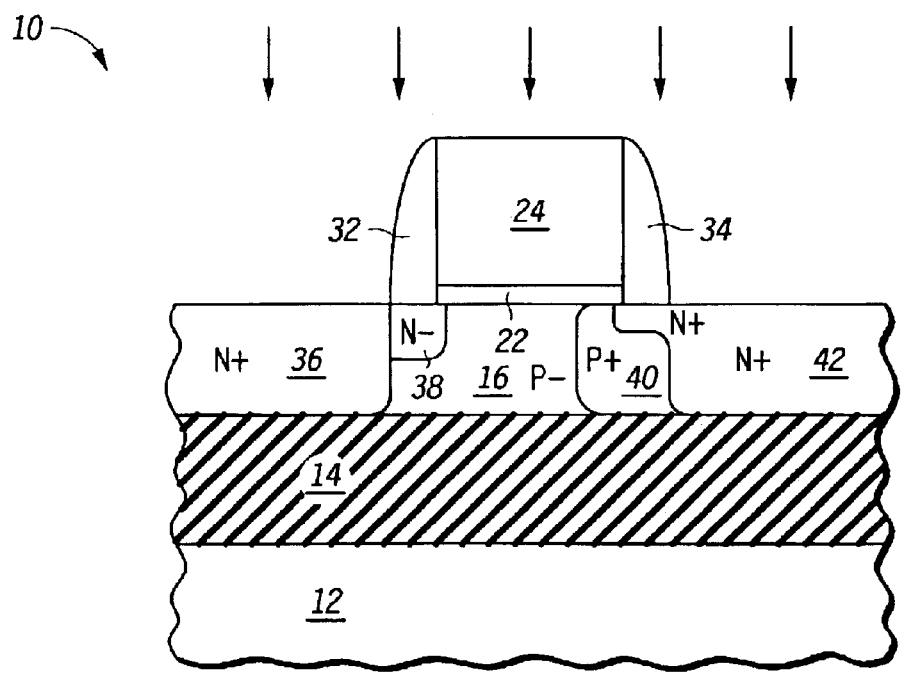

Shown in FIG. 4 is device structure 10 after formation of sidewall spacers 32 and 34 on opposing sides of gate 24 and after an implant using gate 24 and sidewall spacers 32 and 34 as a mask. This implant forms region 36 adjacent to sidewall spacer 32 and region 42 having a shallow portion under sidewall spacer 34 and a major portion substantially aligned with sidewall spacer 34. This is a heavy, deep N-type implant to establish the heavy doping for source and drain contacts. This resulting structure is an essentially completed single transistor DRAM cell. It is understood that in the processing described for FIGS. 1–4, there may many other steps such as performing sacrificial oxide steps and other heating and cleaning steps that are common in semiconductor processing. For example, a thin layer that is subsequently removed may be formed prior to one or more of the implant steps. The resulting structure from this implanting and the heating steps is that doped region 27 of FIG. 3 has a remaining portion that is region 40 in FIG. 4. This region 40, that is doped to P+ and thus at a greater concentration than body 16, extends to insulator 14 and is not only adjacent to region 42 but is contiguous with region 42. Further region 40 is between body 16 where channel current flows and region 42. Region 38 shown in FIG. 4 is a remaining portion of region 18 shown in FIG. 3. Region 36 extends to insulator 14. Region 38 is not only adjacent to region 36 and body 16 but shares one contiguous border with region 36 and another contiguous border with body 16.

In operation, a write is performed by applying a positive gate voltage to gate 24, a greater voltage to region 42, and a lower voltage, preferably ground, to region 36. This establishes electron flow from region 36 to region 42. Due to the presence of region 40 with the relatively higher concentration, impact ionization is increased compared to the impact ionization if there was not the higher doped region, region 40, in the channel current path, which is the region immediately under gate dielectric 22. Current, by convention, is in the opposite direction of the electron flow. This impact ionization, the creation of electron/hole pairs due to the energy of the electrons arriving at region 42, results in excess holes because the electrons are collected by region 42, which is the drain in this scheme of operation. The doping levels of body 16 and doped region 40 are chosen so that the turn-on voltage of the PN junction formed thereacross is not reached during the write. Thus, the diode current for collecting holes is held low during the electron/hole pair formation caused by impact ionization.

An erase is performed by increasing the gate voltage to the voltage near or above the voltage at region 42. This causes a decrease in impact ionization because the lateral electric field is reduced as the gate voltage approaches the drain voltage. This gate voltage, however, also increases the body potential. This then has the effect of increasing the drive on the holes toward region 38. The current from body 16 to region 38 includes the collection of holes. Region 38 has a lower concentration than region 36 to increase the hole flow. The erase mechanism can be viewed as removing holes through diode current, which is current through a forward-biased PN junction. This diode current is increased when the doping of either or both of the P and N regions are decreased. With the higher gate voltage, body 16 increases sufficiently in voltage to pass the turn on voltage of the PN junction between body 16 and region 38. The lower concentration of region 38 thus provides for a larger diode current.

Thus, the P+ region in the channel current path, between the body and the drain contact, beneficially increases impact ionization for writing, and the lower doped region that forms a PN junction with the body and is coupled to the source contact, beneficially increases diode current for erase. In this case writing is considered causing the memory cell to have a lower threshold voltage and erasing is considered causing the memory cell to have a higher threshold voltage. In both cases it is causing the cell to reach a predetermined state.

Figure 5:
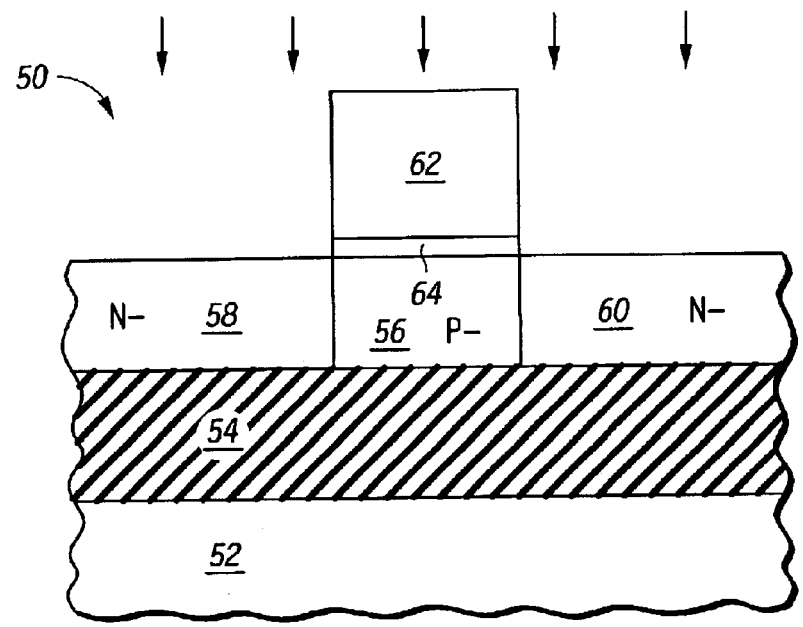
FIGS. 5–9 illustrate sequential cross sectional views of a similar device structure made in accordance with a second embodiment of the present invention.

An alternative structure is shown in various stages of processing in FIGS. 5–8. In FIG. 5 is a device structure 50 comprising an SOI substrate having body region 56 over an insulator 54 and a substrate 52 under insulator 54. Over body region 56 are gate 62 and gate dielectric 64 under gate 62. Regions 58 and 60 are adjacent to body region 56 and substantially aligned to gate 62. Regions 58 and 60 are formed by implanting using gate 62 as a mask. This is a deep but light N type implant to form regions of N−. Regions 58 and 60 extend to insulator 54.

Figure 6:
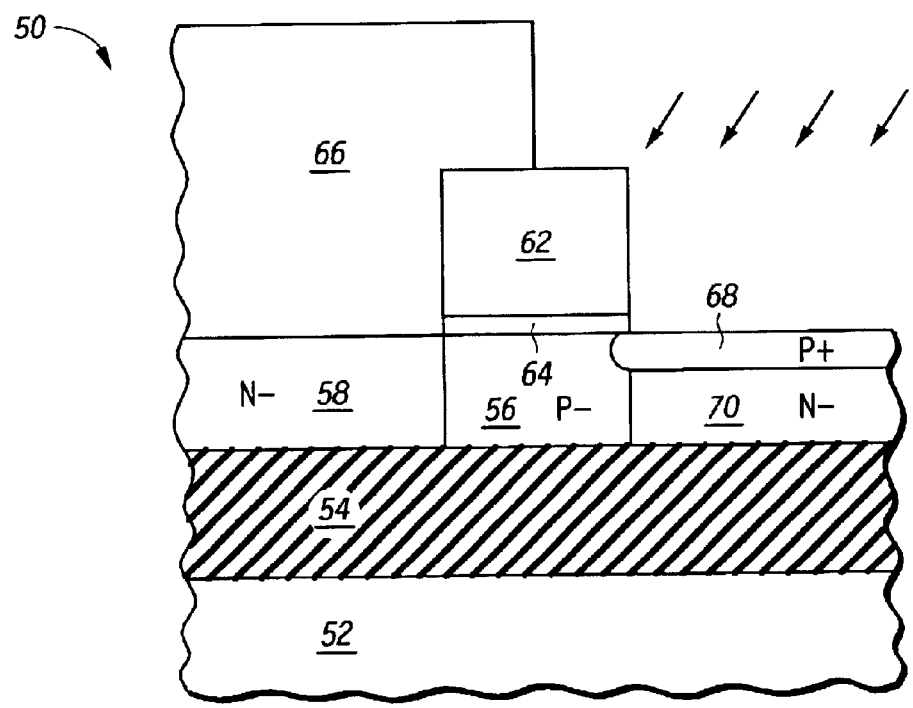

Shown in FIG. 6 is device structure 50 after formation of a mask 66 over a portion of gate 62 and over region 58. A relatively heavy but shallow P-type implant is performed similar to a halo implant. This results in a region 68 of P-type underlapping gate 62. This shallow implant leaves a region 70 which is a portion of region 60 of FIG. 5. Region 68 extends past region 70 into body 56.

Figure 7:
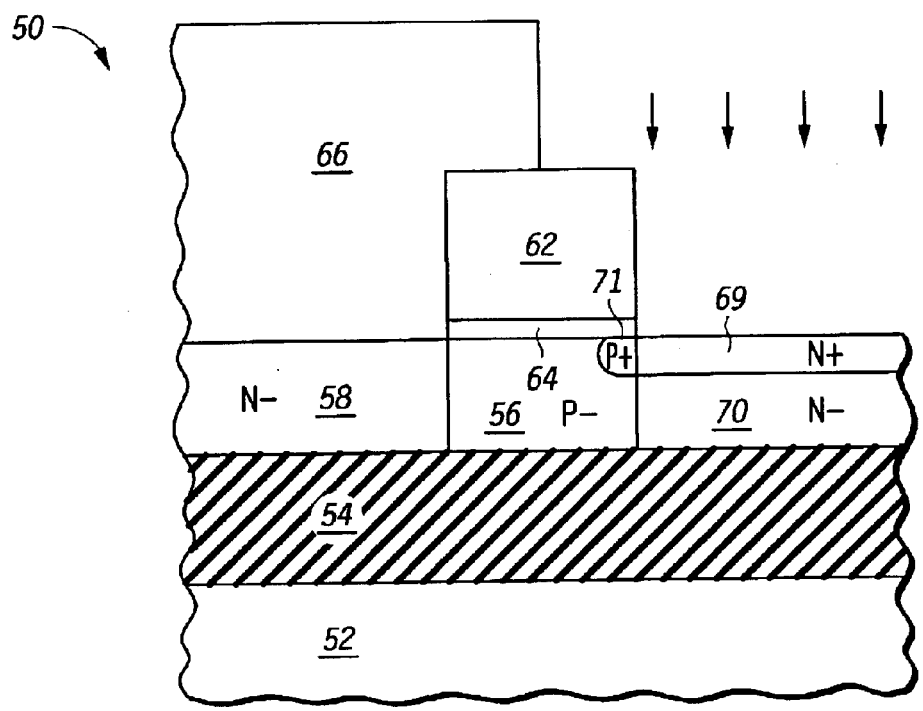

Shown in FIG. 7 is device structure 50 after a shallow, heavy N-type implant. This is a vertical implant that causes most of region 68 of FIG. 6 to be N+. This newly formed N-type region is shown as region 69 in FIG. 7. The portion of region of 68 of FIG. 7 that extends under gate 62 remains as heavily-doped P-type and is shown as region 71. As an alternative or an enhancement, a germanium implant could be performed using mask 66. This germanium implant would lower the bandgap of the resulting PN junction, lowering the turn-on voltage.

Figure 8:
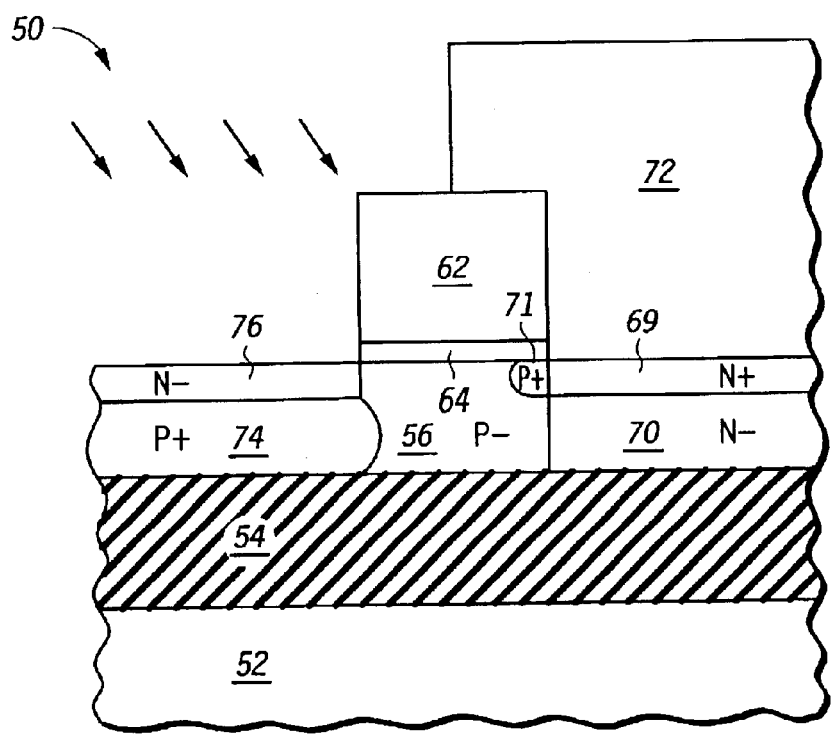

Shown in FIG. 8 is device structure 50 after formation of a mask 72 over a portion of gate 62 and region 69 and a heavy and deep implant. This can be performed as a conventional halo implant in that the implant is heavy, deep, but does not extend to the surface. Region 74 is under a region 76, which is a portion of region 58 shown in FIG. 6. Region 74 extends further into body 56 and thereby further under gate 62 than region 76.

Figure 9:
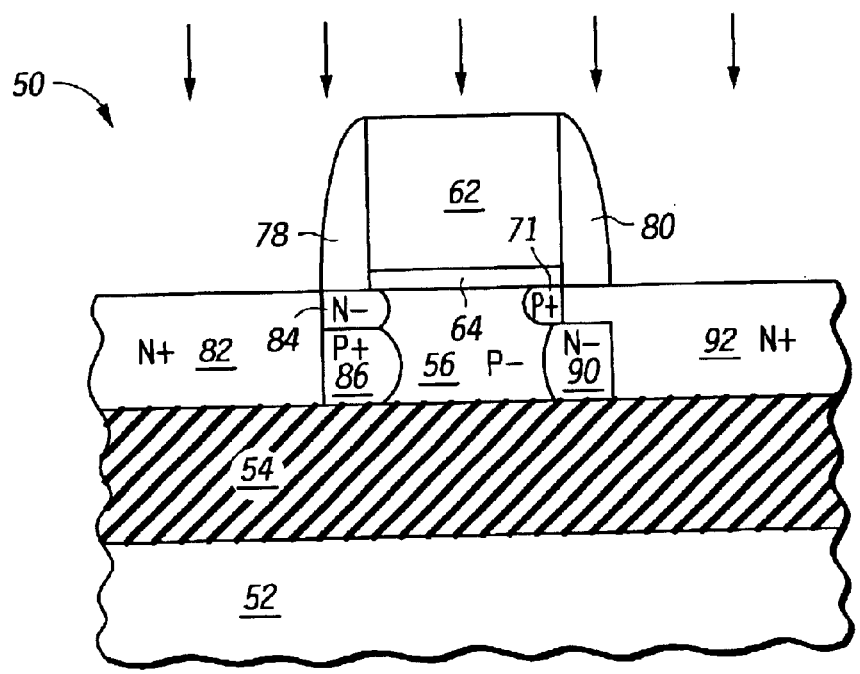

Shown in FIG. 9 is device structure 50 after formation sidewall spacers 78 and 80 on opposing sides of gate 62 and after performance of a heavy and deep N-type implant. This implant forms regions 82 and 92 substantially aligned to sidewall spacers 78 and 80, respectively. Regions 82 and 92 are heavily doped and designated N+. This implant leaves a region 84, which is a portion of region 76 of FIG. 8, and a region 86, which is a portion of region 74 of FIG. 8. This implant also leaves a region 90 which is a small remaining portion of region 70 of FIG. 8.

For writing, gate 62 is at a positive voltage, region 92 is at a higher voltage and region 82 is at a lower voltage. In such case channel current must pass through region 71 so that electrons coming from region 84 will pass through heavily doped region 71 causing increased impact ionization. For an erase, the voltage is reversed so that the higher voltage is at region 82 and the lower voltage is at region 92. This reverses the source and the drain. The gate voltage is increased from that applied for writing. This channel current still passes through region 71 but this is now at the low voltage end and also passes through region 84 at the high voltage end so that minimal impact ionization occurs. The region 90, being lightly doped, provides the increased diode current. Thus, there is both the increased diode current for the erase case with the N− region adjacent to the body and the source contact region and increased impact ionization during a write with the P+ region between the channel and the drain contact region.

FIGS. 10–13 show a third embodiment that has the benefits of highly doped region of the same type as the body and lesser doped region of the same conductivity type as the source and drain contacts for assisting with writing and erasing a capacitorless DRAM cell.

Figure 10:
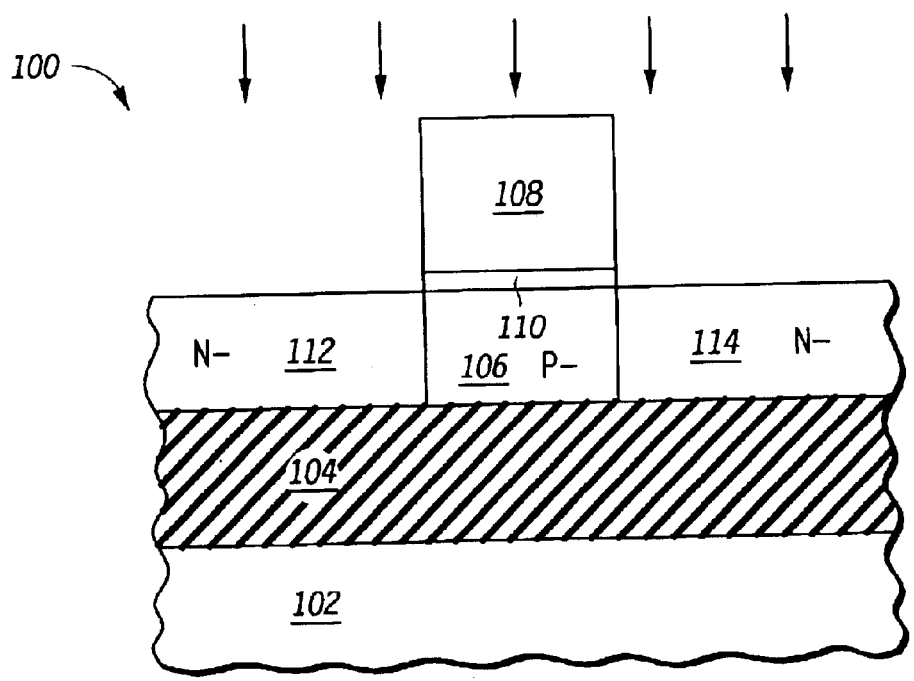
FIGS. 10–13 illustrate sequential cross sectional views of a similar device structure made in accordance with a third embodiment of the present invention.

Shown in FIG. 10 is a device structure 100 similar to FIG. 5 comprising an SOI substrate having body region 106 over an insulator 104 and a substrate 102 under insulator 104. Over body region 106 are gate 108 and gate dielectric 110 under gate 108. Regions 112 and 114 are adjacent to body region 106 and substantially aligned to gate 108. Regions 112 and 114 are formed by implanting using gate 108 as a mask. This is a deep but light N type implant to form N-type regions of N−. Regions 112 and 114 extend to insulator 104.

Figure 11:
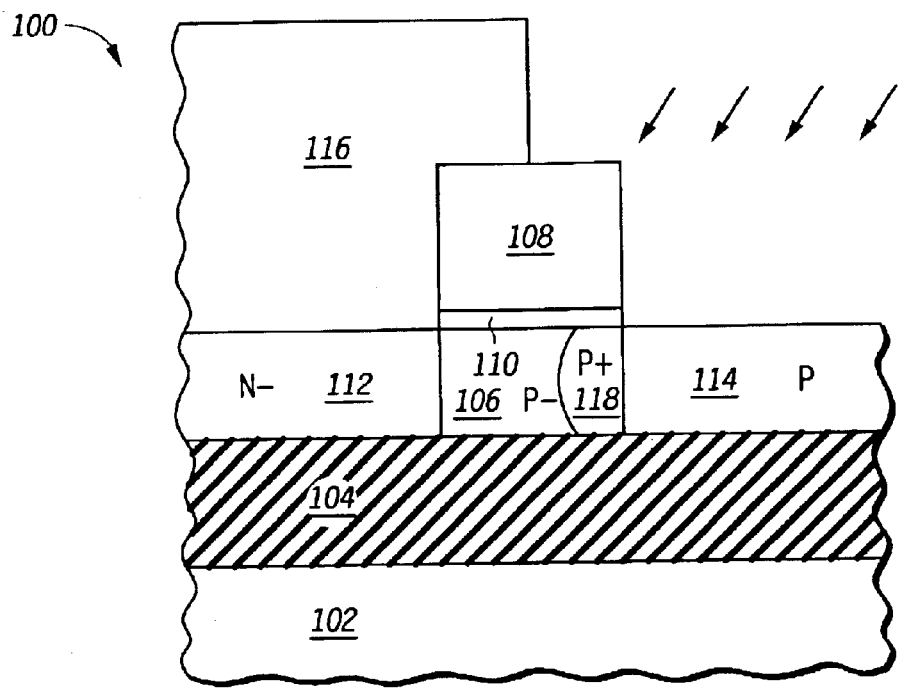

Shown in FIG. 11 is device structure 100 after formation of a mask 116 that covers region 112 and a portion of gate 108 and after an angled implant that is both heavy and deep. In this case the energy of the implant is varied to extend from the surface of body 106 to insulator 104 and extend from region 114 into body 106 to form region 118 that is P+and underlaps gate 108. This angled implant also converts region 114 that is shown as P after the implant.

Figure 12:
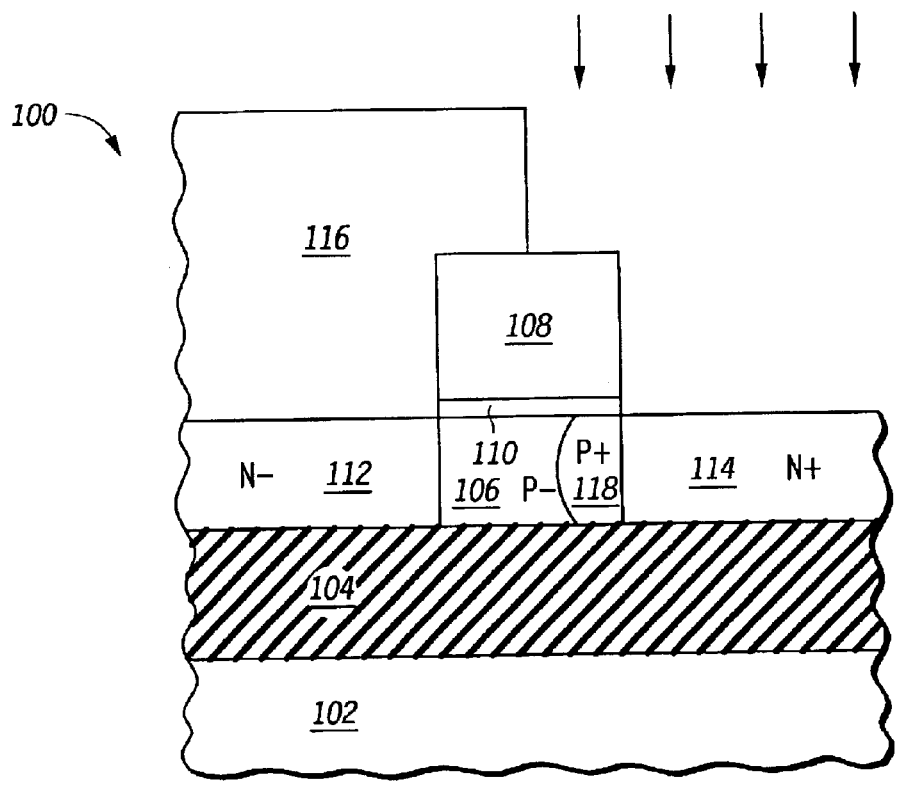

Shown in FIG. 12 is device structure 100 after a vertical implant of N type using mask 116 that converts region 114 back to N-type but more heavily doped.

Figure 13:
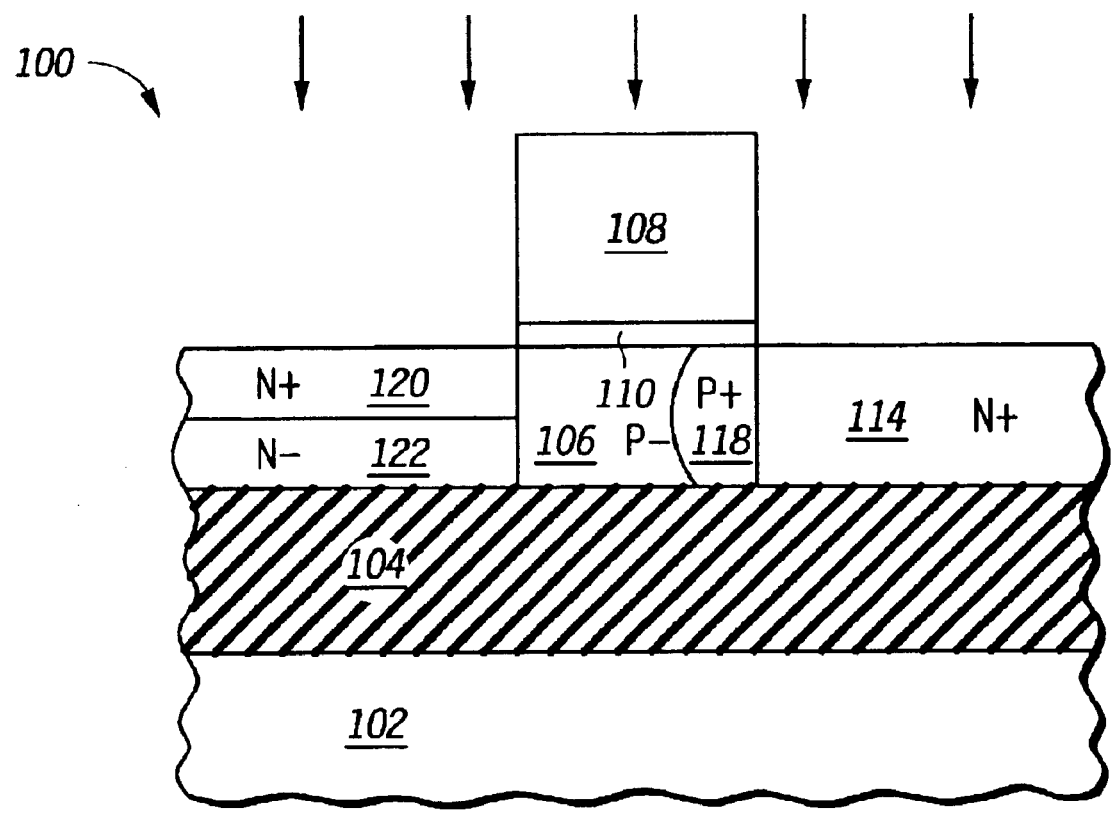

Shown in FIG. 13 is device structure 100 after an implant using gate 108 as a mask. This is a relatively shallow implant to form region 120 to N+. Region 122 is a remaining portion region 112 of FIG. 12 that remains after the implant. This implant establishes a heavily doped contact region. This resulting structure is a DRAM cell that may be written by impact ionization and be erased by diode current.

In operation a write is achieved with a positive voltage on gate 108, a higher voltage on region 114, and a lesser voltage on region 120. The channel current path must pass through heavily doped region P+ on the drain side and thus provide the benefit of relatively high impact ionization. For the erase, the gate voltage is increased lowering the lateral field and thus reducing impact ionization while increasing diode current to region 120. Lower doped region 122 provides the increased diode current that benefits erase.

In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential feature or element of any or all the claims. The terms P−, N−, P, N, P+, and N+ are used to indicate the relative doping levels. For example, the P− body is preferably in the 1e17 to 5e17 range. The N− will be somewhat similar at around the 1e17 to 3e17 range. In other applications, P− and N− may be considered lowered concentrations, such is as 1e15 to 1e16. Of course, the concentrations can vary greatly as the device is optimized in the particular fabrication process that is chosen.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A one-transistor dynamic random access memory (DRAM) cell comprising:
   a transistor having a first drain/source region, a second drain/source region, a body region between the first and second drain/source regions, and a gate over the body region, wherein a doping concentration of a portion of the first drain/source region adjacent to the body region is different than a doping concentration of a portion of the second drain/source region adjacent to the body region.

2. The DRAM cell of claim 1, wherein the portions of the first and second drain/source regions are located relatively near to the gate.

3. The DRAM cell of claim 1, further comprising a halo region between the body region and the first drain/source region.

4. The DRAM cell of claim 3 wherein impact ionization is used to transfer charge to the body region for lowering a threshold voltage of the transistor to write a first state during a write operation of the DRAM cell.

5. The DRAM cell of claim 4, wherein the first drain/source region is relatively heavily doped and the threshold voltage is lowered during the write operation in response to a high potential applied to the heavily doped drain/source region, a low potential to the second drain/source region, and a gate potential that is between the low and high potentials.

6. The DRAM cell of claim 3, wherein a drain/source diode is used to remove charge from the body region to raise a threshold voltage of the transistor to write a second state during a write operation of the DRAM cell.

7. The DRAM cell of claim 6, wherein the first drain/source region is relatively heavily doped and the threshold voltage is raised during a write operation in response to a high potential applied to the heavily doped drain/source region, a low potential to the second drain/source region, and a high gate potential.

8. The DRAM cell of claim 2 wherein the second drain/source region includes Germanium.

9. The DRAM cell of claim 1, wherein the transistor is characterized as being a silicon-on-insulator (SOI) N-channel transistor.

10. A one-transistor dynamic random access memory (DRAM) cell comprising:
    a transistor having a first drain/source region, a second drain/source region, a body region between the first and second drain/source regions, and a gate over the body region, wherein a doping concentration of an area of the body region directly adjacent to the first drain/source region has a different doping concentration than an area of the body region directly adjacent to the second drain/source region.

11. The DRAM cell of claim 10, wherein the transistor is characterized as being a silicon-on-insulator (SOI) N-channel transistor.

12. The DRAM cell of claim 10, wherein the area of the body region directly adjacent to the first drain/source region is a halo region.

13. The DRAM cell of claim 12, further comprising an area located between the body region and the first drain/source region and under the halo that includes Germanium.

14. The DRAM cell of claim 10 wherein impact ionization is used to transfer charge to the body region for lowering a threshold voltage of the transistor to write a first state to the DRAM cell during a write operation.

15. The DRAM cell of claim 14, wherein the first drain/source region is relatively heavily doped and the threshold voltage is lowered during the write operation in response to a high potential applied to the heavily doped drain/source region, a low potential to the second drain/source region, and a gate potential that is between the low and high potentials.

16. The DRAM cell of claim 10, wherein a drain/source diode is used to remove charge from the body region to raise a threshold voltage of the transistor to write a second state during a write operation of the DRAM cell.

17. The DRAM cell of claim 16, wherein the first drain/source region is relatively heavily doped and the threshold voltage is raised during a write operation in response to a high potential applied to the heavily doped drain/source region, a low potential to the second drain/source region, and a high gate potential.

18. A one-transistor dynamic random access memory (DRAM) cell comprising:
    a transistor having a first drain/source region, a second drain/source region, a body region between the first and second drain/source regions, and a gate over the body region, wherein a doping concentration of a first area of the body region directly adjacent to the first drain/ source region has a different doping concentration than a second area of the body region directly adjacent to the second drain/source region, and wherein a doping concentration of a portion of the first drain/source region adjacent to the body region is different than a doping concentration of a portion of the second drain/source region adjacent to the body region.

19. The DRAM cell of claim 18, wherein the transistor is characterized as being a silicon-on-insulator (SOI) N-channel transistor.

20. The DRAM cell of claim 19, wherein the area of the body region directly adjacent to the first drain/source region is a halo region.

21. The DRAM cell of claim 20, further comprising an area located between the body region and the first drain/source region and under the halo that includes Germanium.

22. The DRAM cell of claim 18 wherein impact ionization is used to transfer charge to the body region for lowering a threshold voltage of the transistor to write a first state to the DRAM cell during a write operation.

23. The DRAM cell of claim 22, wherein the first drain/source region is relatively heavily doped and the threshold voltage is lowered during the write operation in response to a high potential applied to the heavily doped drain/source region, a low potential to the second drain/source region, and a gate potential that is between the low and high potentials.

24. The DRAM cell of claim 18, wherein a drain/source diode is used to remove charge from the body region to raise a threshold voltage of the transistor to write a second state during a write operation of the DRAM cell.

25. The DRAM cell of claim 24, wherein the first drain/source region is relatively heavily doped and the threshold voltage is raised during a write operation in response to a high potential applied to the heavily doped drain/source region, a low potential to the second drain/source region, and a high gate potential.

26. A method for forming a one-transistor dynamic random access memory (DRAM) cell, comprising the steps of:

providing a silicon-on-insulator (SOI) semiconductor device having an insulator formed on a substrate and a semiconductor layer formed on the insulator;

forming a body region of the memory cell in the semiconductor layer;

forming a gate over the body region;

forming first and second drain/source regions in the semiconductor layer adjacent to, and on opposite sides of, the body region;

forming a halo region in the body region adjacent to the first drain/source region;

forming a heavily doped extension in the first drain/source region underlapping the gate; and forming a lightly doped extension in the second drain/source region underlapping the gate.

27. The method of claim 26, wherein the body region is P-type and the first and second drain/source regions are N-type.

28. The method of claim 26, wherein the halo region is P-type, the heavily doped extension is N-type, and the lightly doped extension is N-type.

29. A method for forming a one-transistor dynamic random access memory (DRAM) cell, comprising the steps of:

providing a silicon-on-insulator (SOI) semiconductor device having an insulator formed on a substrate and a semiconductor layer formed on the insulator;

forming a body region of the memory cell in the semiconductor layer;

forming a gate over the body region;

forming first and second drain/source regions in the semiconductor layer adjacent to, and on opposite sides of, the body region;

forming a first halo region in the body region adjacent to the first drain/source region and to the gate; and forming a second halo region in the body region adjacent to the second drain/source region and to the insulator.

30. The method of claim 29, further comprising a first lightly doped extension formed under the first halo region and adjacent to first drain/source region.

31. The method of claim 29, further comprising a second lightly doped extension formed over the second halo region and adjacent to the second drain/source region.

32. A method for forming a one-transistor dynamic random access memory (DRAM) cell, comprising the steps of:

providing a silicon-on-insulator (SOI) semiconductor device having an insulator formed on a substrate and a semiconductor layer formed on the insulator, the semiconductor layer having a surface;

forming a body region of the memory cell in the semiconductor layer;

forming a gate over the body region on the surface of the semiconductor layer;

forming first and second drain/source regions in the semiconductor layer adjacent to, and on opposite sides of, the body region;

forming a halo region in the body region adjacent to the first drain/source region and to the gate;

heavily doping the first drain/source region; and heavily doping a portion of the second drain/source region, the portion being near the surface of the semiconductor layer.

* * * * *